US012163977B2

(12) United States Patent
Zeinstra et al.

(10) Patent No.: US 12,163,977 B2
(45) Date of Patent: Dec. 10, 2024

(54) BODY POSITION DETECTION

(71) Applicant: KONINKLIJKE PHILIPS N.V., Eindhoven (NL)

(72) Inventors: Michiel Hans Zeinstra, Blauwhuis (NL); Petrus Johannes Bremer, Drachten (NL); Jeroen Beutick, Zwolle (NL); Frank Van Der Schoot, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 353 days.

(21) Appl. No.: 17/849,772

(22) Filed: Jun. 27, 2022

(65) Prior Publication Data
US 2023/0003761 A1    Jan. 5, 2023

(30) Foreign Application Priority Data
Jun. 30, 2021 (EP) ..................................... 21182764

(51) Int. Cl.
*G01P 15/18* (2013.01)
*A61B 5/11* (2006.01)
*G06F 3/01* (2006.01)

(52) U.S. Cl.
CPC ............ *G01P 15/18* (2013.01); *A61B 5/1114* (2013.01); *G06F 3/011* (2013.01); *A61B 2562/0219* (2013.01)

(58) Field of Classification Search
CPC ................... G01P 15/18; A61B 5/1114; A61B 2562/0219; A61B 5/4809; A61B 5/1126; A61B 5/1116; G06F 3/011
See application file for complete search history.

(56) References Cited

U.S. PATENT DOCUMENTS 10,441,197 B2 * 10/2019 Thein .................... A61B 5/1123
2012/0232823 A1 * 9/2012 Baggen .............. G08B 21/0446
702/141
(Continued)

FOREIGN PATENT DOCUMENTS

CN    108852289 A    11/2018
CN    109171655 A  *  1/2019
(Continued)

OTHER PUBLICATIONS

Pedley, Mark "Tilt Sensing Using a Three-Axis Accelerometer", Freescale Semiconductor Application Note Document No. AN3461 Rev. 6, Mar. 2013.

*Primary Examiner* — Francis C Gray
(74) *Attorney, Agent, or Firm* — Michael W. Haas

(57) ABSTRACT

The present invention relates to body position detection. In order to improve body position detection, a computer-implemented method is provided that comprises the steps of:
a) receiving (210) accelerometer data from an accelerometer mounted on a user,
wherein the received accelerometer data comprises three acceleration components including a first acceleration component in a first axis direction, a second acceleration component in a second axis direction substantially perpendicular to the first axis direction, and a third acceleration component in a third axis direction substantially perpendicular to a plane formed by the first and second axes; and
wherein the first axis direction is parallel to a frontal axis of the user, the second axis direction is parallel to a longitudinal axis of the user, and the third axis direction is parallel to a sagittal axis of the user;
b) determining (220), based on the received accelerometer data, at least one body position based on a comparison between an absolute value of a projection of a gravity vector on a plane formed by two of the first, second, and (Continued)

third axes and an absolute value of an acceleration component in a remaining axis direction.

15 Claims, 7 Drawing Sheets

(56) References Cited

U.S. PATENT DOCUMENTS

2013/0116602 A1* 5/2013 Van Den Heuvel ......................... A61B 5/1126 600/595
2014/0335490 A1  11/2014 Baarman

FOREIGN PATENT DOCUMENTS

| DE | 102009046775 A1 * | 5/2011 | ........... A61B 5/1114 |
| KR | 101996563 B1 * | 4/2017 | |

* cited by examiner

BODY POSITION DETECTION

FIELD OF THE INVENTION

The present invention relates to body position detection. In particular, the present invention relates to a computer-implemented method and an apparatus for body position detection, to a body detection system, to a computer program product, and to a computer-readable data carrier.

BACKGROUND OF THE INVENTION

Accelerometers are often used to calculate a tilt angle. They can only do this reliably when they are static and not moving. Trigonometry calculations are often used to obtain the angle from the raw values from trigonometry calculations and matrix operations. These calculations typically require sinus, cosine, and/or tangent calculations and complex matrix operations, which usually require relatively high processing power.

SUMMARY OF THE INVENTION

There may be a need to provide an improved body position detection method and device.

The object of the present invention is solved by the subject-matter of the independent claims. Further embodiments and advantages of the invention are incorporated in the dependent claims. Furthermore, it shall be noted that all embodiments of the present invention concerning a computer-implemented method might be carried out with the order of the steps as described, nevertheless this has not to be the only and essential order of the steps of the method as presented herein. The computer-implemented method disclosed herein can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to a first aspect of the present invention, there is provided a computer-implemented method for body position detection, comprising the steps of:
a) receiving accelerometer data from an accelerometer mounted on a user,
   wherein the received accelerometer data comprises three acceleration components including a first acceleration component in a first axis direction, a second acceleration component in a second axis direction substantially perpendicular to the first axis direction, and a third acceleration component in a third axis direction substantially perpendicular to a plane formed by the first and second axes; and
   wherein the first axis direction is parallel to a frontal axis of the user, the second axis direction is parallel to a longitudinal axis of the user, and the third axis direction is parallel to a sagittal axis of the user;
b) determining, based on the received accelerometer data, at least one body position based on a comparison between an absolute value of a projection of a gravity vector on a plane formed by two of the first, second, and third axes and an absolute value of an acceleration component in a remaining axis direction.

The inventors of the present disclosure have found out that trigonometry calculations and complex matrix operations require a relatively high calculation effort by a microcontroller. The inventors of the present disclosure have also found out that detecting the body position based on the projected length of the gravity on another vector of the accelerometer coordinate system may cause position detection issues when the accelerometer coordinate system is tilted.

Towards this end, a computer-implemented method is proposed that detects at least one body position by the use of an accelerometer by means of comparing an absolute value of a projection of a gravity vector on a plane with an absolute value of the other axis. In some examples, certain body positions may be determined by comparing absolute values of two of the three acceleration components, and/or determining a sign of a value of one of the three acceleration components. By this approach, no trigonometry functions are required. This approach may reduce the calculation power compared with conventional trigonometry functions, in particular for position detection when the accelerometer coordinate system is tilted.

According to an embodiment of the present invention, the body position comprises a sleeping position and a non-sleeping position. Step b) further comprises the step of determining whether the user is in a sleeping position or in a non-sleeping position based on a comparison between an absolute value of the projection of the gravity vector on the plane formed by the first and third axis directions and an absolute value of the second acceleration component.

In other words, in order to detect that a user is going from any sleeping position to a non-sleeping position, the value of the plane is compared with the value of the other axis. For example in sleeping position, the vector $\sqrt{A_x^2+A_z^2}$ will be equal to 1 G, independent if the user is in a supine, prone, left, or right position. The second acceleration component $A_y$ will be zero, since this axis is horizontal with respect to the earth. When the user goes to standing, the vector $\sqrt{A_x^2+A_z^2}$ will decrease and the absolute value of $A_y$ will increase. A toggle moment may be defined by means of a threshold, for example when $|A_y|>\sqrt{A_x^2+A_z^2}$, which is at 45°.

According to an embodiment of the present invention, the absolute value of the second acceleration component is multiplied by a tangent of a desired angle for the comparison. In order to remain flexible on the angle of toggling, it is also proposed to multiply the threshold by the tangent of a desired angle. This will be explained hereafter and in particular with respect to the embodiment shown in FIG. 6.

According to an embodiment of the present invention, when it is determined that the user is in a non-sleeping position, the method further comprises the step of determining, based on a sign of a value of the second acceleration component, whether the user is in a standing or an upside-down position.

In other words, in order to distinguish between upside down and standing positions, the system can look at the value of the y-axis. When $A_y$ is positive, the user is in a standing position and when $A_y$ is negative, the user is in an upside-down position. This will be explained hereafter and in particular with respect to the embodiment shown in FIG. 7.

According to an embodiment of the present invention, when it is determined that the user is in a sleeping position, the method further comprises the step of determining whether the user is in a flat position or in a side position based on (i) a comparison between an absolute value of the third acceleration component with an absolute value of the first acceleration component, or (ii) a comparison between an absolute value of a projection of a gravity vector on a plane formed by the second and third axes and an absolute value of the first acceleration component.

This will be explained hereafter and in particular with respect to the embodiments shown in FIGS. 8 and 9.

According to an embodiment of the present invention, the absolute value of the first acceleration component is multiplied by a tangent of a desired angle for the comparison.

This will be explained hereafter and in particular with respect to the embodiment shown in FIG. 9.

According to an embodiment of the present invention, when it is determined that the user is in a side position, the method further comprises the step of determining, based on a sign of a value of the first acceleration component, whether the user is in a left or right position.

This will be explained hereafter and in particular with respect to the embodiment shown in FIG. 10.

According to an embodiment of the present invention, when it is determined that the user is in a flat position, the method further comprises the step of determining, based on a sign of a value of the third acceleration component, whether the user is in a supine or prone position.

This will be explained hereafter and in particular with respect to the embodiment shown in FIG. 11.

According to an embodiment of the present invention, the method further comprises the steps of detecting, based on the received accelerometer data, a movement of the user, and determining the body position of the user using an unfiltered value of the three acceleration components, if the movement is below a pre-defined threshold.

The inventors of the present disclosure have found out that moving from one sleeping position to an opposite sleeping position (180°) within quickly may cause a wrong position detection when filtering (or averaging) of samples is applied. For example, rotating device from position 'supine' to position 'prone' within 1 second may cause a wrong position detection and a side position could be signalled to the system.

To prevent false position detection by filtering, movement detection is applied instead of filtering. When movement is below a threshold, new position is calculated based on unfiltered values. This will be explained hereafter and in particular with respect to the embodiments shown in FIGS. 13 and 14.

According to an embodiment of the present invention, the detection of the movement of the user further comprises the steps of calculating a resultant vector of the three acceleration components, and determining that the user is moving when the resultant vector exceeds a moving threshold.

According to an embodiment of the present invention, the detection of the movement of the user further comprises the steps of calculating an average of a plurality of consecutive samples that are within a certain range of a moving average for each of the three acceleration components, calculating, for each sample, a difference between a sample value of the respective sample and the average, and determining that the user is moving when one or more sample values exceed a threshold from the moving average.

This will be explained hereafter and in particular with respect to the embodiments shown in FIGS. 13 and 14.

According to a second aspect of the present invention, there is provided an apparatus comprising a communications module configured to receive accelerometer data from an accelerometer mounted on a user, and a processing unit configured to perform the steps of the method according to the first aspect and any associated example.

According to a third aspect of the present invention, there is provided a body position detection system, which comprises an accelerometer mountable on a user, and a data processing apparatus according to the second aspect and any associated example.

According to a further aspect of the present invention, there is provided a computer program product comprising instructions instructions to cause the apparatus of the second aspect or the body position detection system of the third aspect to execute the steps of the method according to the first aspect and any associated example.

According to another aspect of the present invention, there is provided a computer-readable data carrier having stored thereon the computer program product.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF THE EMBODIMENTS

Figure 1:
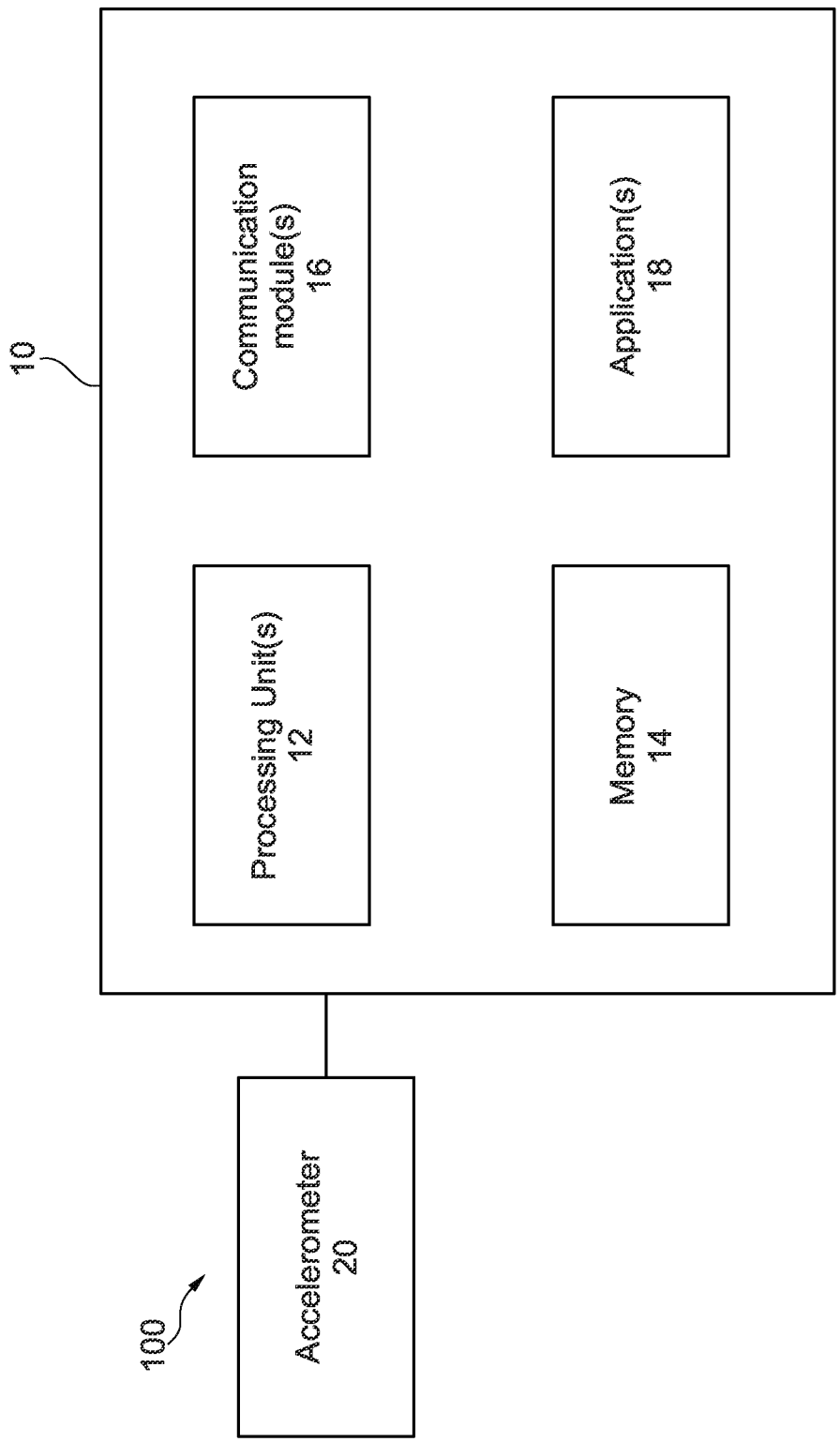
FIG. 1 shows a block diagram of an exemplary apparatus for body position detection.

FIG. 1 illustrates a block diagram of an exemplary apparatus 10 for body position detection, in accordance with an embodiment. The apparatus 10 may receive accelerometer data from an accelerometer 20. The apparatus 10 and the accelerometer 20 form a body position detection system 100.

The apparatus 10 may include one or more processing units 12. Optionally, as shown in FIG. 1, the apparatus 10 may include a memory 14, one or more communications modules 16, and one or more applications 18.

In general, the apparatus 10 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 1 may show a limited number of components by way of example, it can be appreciated that a greater or a fewer number of components may be employed for a given implementation.

In some examples, the apparatus 10 may be implemented by a computing platform such as a mobile platform, personal computer (PC) platform, and/or consumer electronics (CE) platform supporting various networking, communications, and/or multimedia capabilities. Such capabilities may be supported by various networks, such as a Wide Area Network (WAN), Local Area Network (LAN), Metropolitan Area Network (MAN), wireless WAN (WWAN), wireless LAN (WLAN), wireless MAN (WMAN), wireless personal area network (WPAN), Worldwide Interoperability for Microwave Access (WiMAX) network, broadband wireless access (BWA) network, the Internet, and/or any other wired or wireless network in accordance with the described embodiments.

In some implementations, the apparatus 10 may comprise a system within and/or coupled to a computing device such as PC, desktop PC, notebook PC, laptop computer, mobile internet device (MID), mobile computing device, smart phone, personal digital assistant (PDA), mobile telephone, or other type of computing device in accordance with the described embodiments. The computing device may include, for example, an electronic display.

In some implementations, the apparatus 10 may be implemented as a sleep position trainer. This sleep position trainer prevents the user sleeping in a predefined position by detection of that position and provide the user feedback. The feedback can be a mechanical actuator, a lighting indication or any other indication that stimulates the user to turn into another sleeping position. The detection of the sleep position and the actuator can be in separate devices connected by any kind of connection system (for example a wireless network).

Returning to FIG. 1, the processing unit(s) 12 may execute instructions to perform the method described herein, which will be explained in detail with respect to the embodiment shown in FIG. 3.

The memory 14 may include, but is not limited to, volatile memory and/or non-volatile memory. The memory 14 may be used to store body positions, processor instructions, and other data and instructions to enable the processor to perform the techniques described herein.

The one or more communications modules 16 may include hardware and/or software to enable the apparatus 10 to receive data from the accelerometer 20, and to communicate with other devices and/or a network. For example, the one or more communications modules 16 may receive accelerometer data via a wired connection or via a wireless connection. The one or more communications modules 16 may also provide cellular telephone communications, and/or other data communications for the apparatus 10.

The one or more applications 18 may include various software and/or hardware-based applications that provide functionality to the apparatus 10. The one or more applications 16 may include an application that orients the accelerometer data. The one or more applications 16 may include, for example, cellular telephone applications, messaging applications, health and fitness applications, etc.

Figure 2:
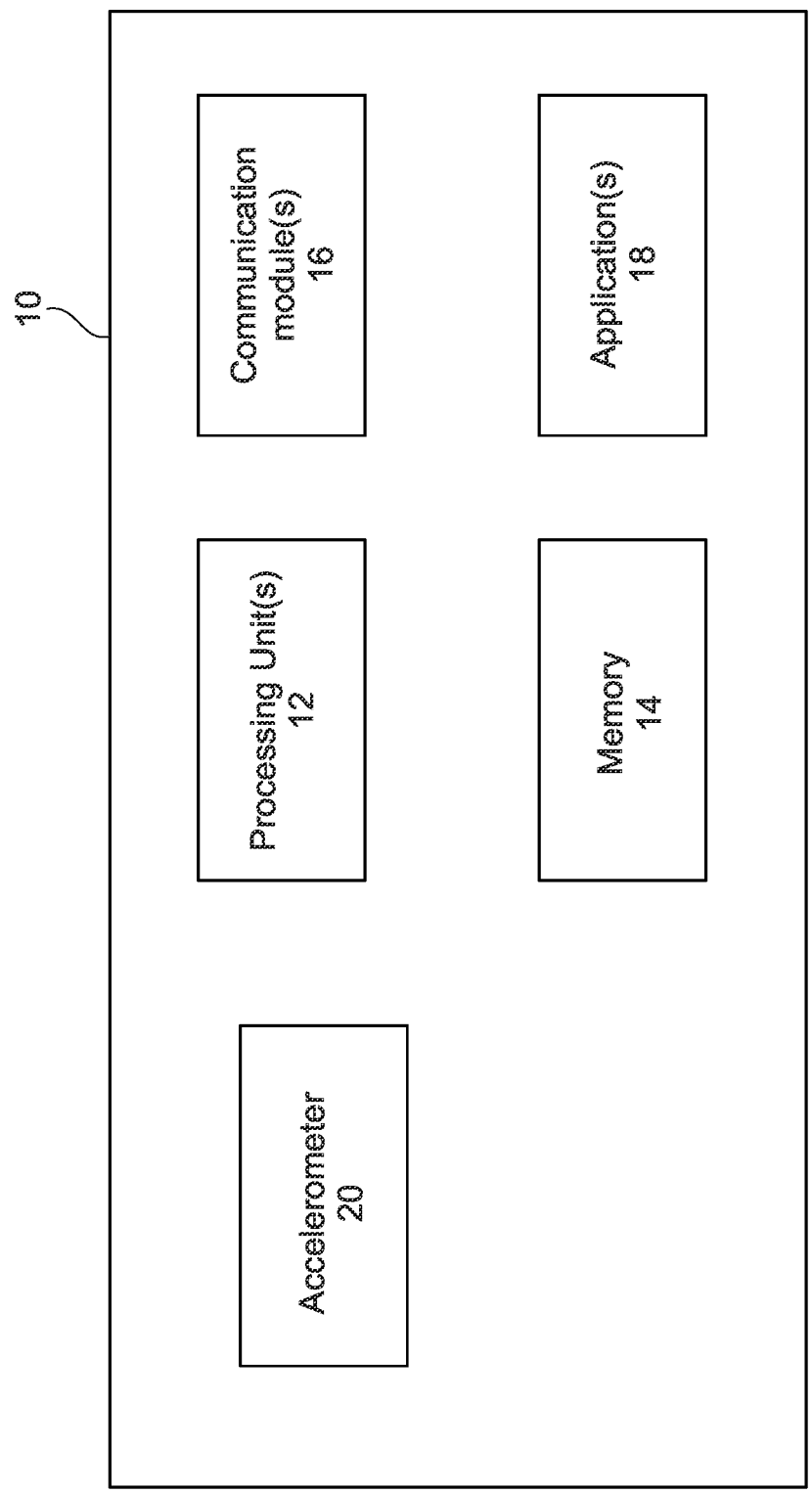
FIG. 2 shows an alternate embodiment of an apparatus.

FIG. 2 illustrates an alternate embodiment of an apparatus 10, where the accelerometer 20 is included within apparatus 10. The apparatus 10 may be substantially functionally equivalent to the system illustrated in FIG. 1.

Figure 3:
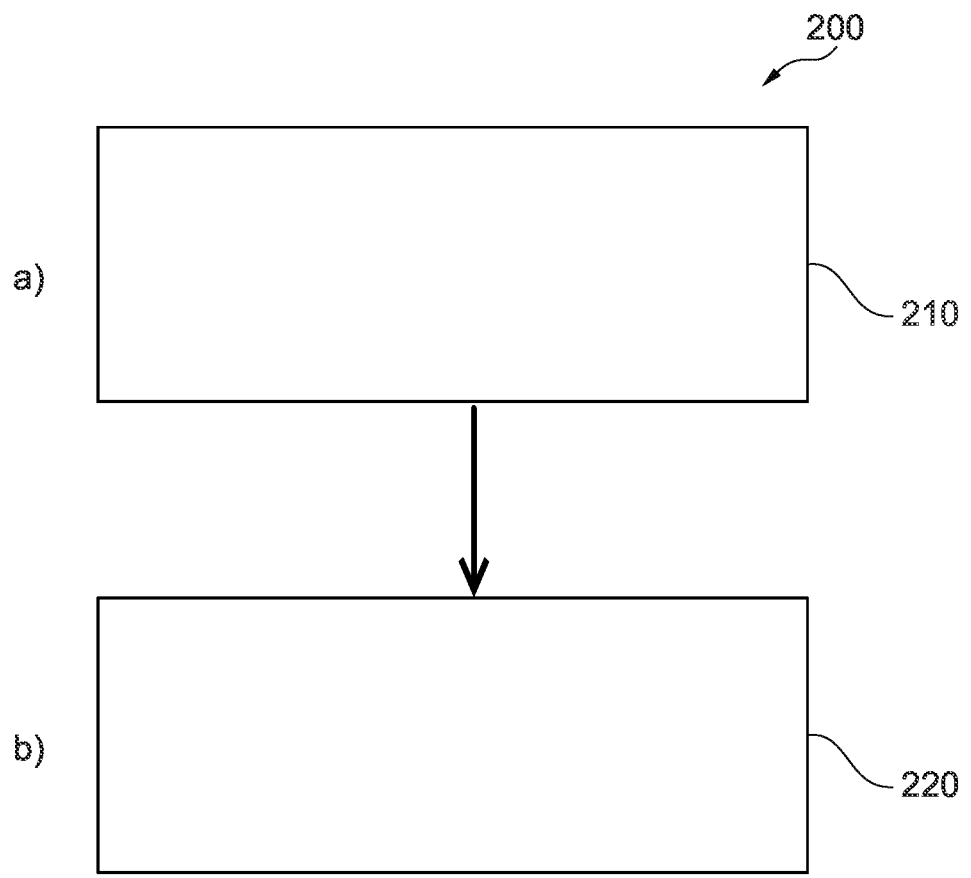
FIG. 3 shows a flow chart describing a computer-implemented method for body position detection.

FIG. 3 illustrates a flow chart describing a computer-implemented method 200 for body position detection, in accordance with an embodiment. Beginning at block 210 i.e. step a), an apparatus, such as apparatus 10 shown in FIG. 1 or in FIG. 2, may receive accelerometer data from an accelerometer mounted on a user in block 120. The accelerometer may be e.g. a waist-mounted accelerometer, a head-mounted accelerometer, a chest-mounted accelerometer, etc. As discussed above, the accelerometer may be separate from the apparatus, or a component of the apparatus.

Figure 4A:
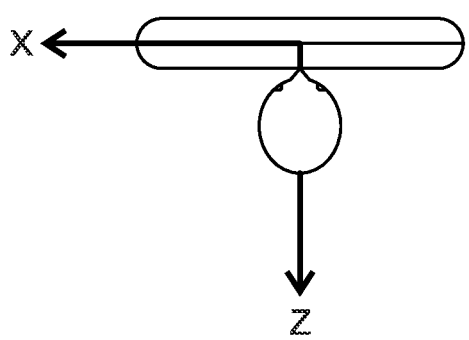
FIGS. 4A and 4B show a coordinate system, as may be defined by an accelerometer-based device.
Figure 4B:
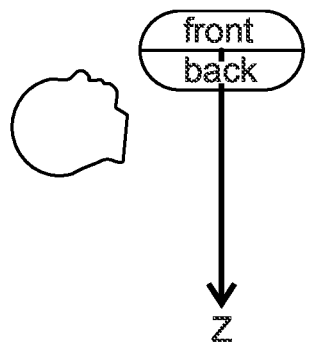

FIGS. 4A and 4B illustrate a coordinate system, as may be defined by an accelerometer-based device. The reference coordinates may define a first axis direction X, a second axis direction Y, and a third axis direction Z. In particular, the first axis direction X is parallel to a frontal axis of a user the second axis direction Y is parallel to a longitudinal axis of the user, and the third axis direction Z is parallel to a sagittal axis of the user. Thus, the received accelerometer data comprises three acceleration components including a first acceleration component $A_x$ in the first axis direction X, a second acceleration component $A_y$ in the second axis direction Y, and a third acceleration component $A_z$ in the third axis direction Z. Embodiments may rotate the observed coordinate system to the above-described reference coordinate system, such that the body position detection algorithm can have a consistent frame of reference.

Turning back to FIG. 3, at block 220, the apparatus processes the received accelerometer data and determines at least one body position based on a comparison between an absolute value of a projection of a gravity vector on a plane formed by two of the first, second, and third axes and an absolute value of an acceleration component in a remaining axis direction. Some body positions may be determined based on a comparison between absolute values of two of the three acceleration components and/or a sign of a value of one of the three acceleration components.

Thus, the body position of a user can be calculated by a simple algorithm. The simple algorithm does not require trigonometric calculations and can be applied to small low power micro controllers without using floating-point. Furthermore, the length of the gravity vector as projected on a plane instead on its perpendicular vector to prevent position detection issues with a tilted accelerometer coordinate system.

In the following, processing methods for determining the body position will be elucidated.

Since one needs to know in which sleeping position the user is, the number of positions is limited. Sleeping positions can be defined as supine, prone, left and right. Besides this, also non-sleep positions can be determined, such as standing and upside down.

Sleeping vs Non-Sleeping Position

Figure 5:
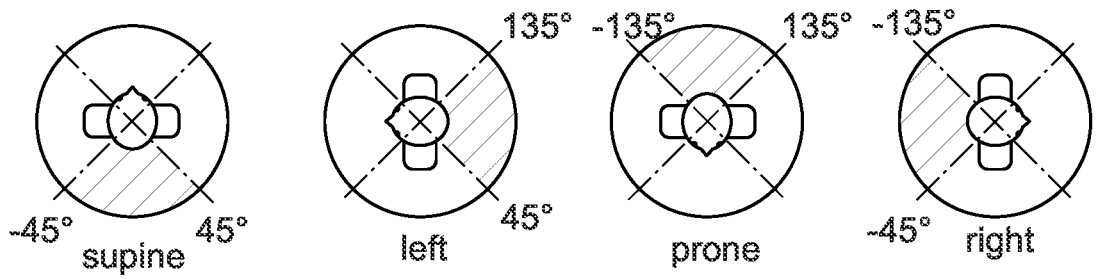
FIG. 5 shows various sleeping positions.

The sleeping position can be detected by the projection of the gravity vector on the plane formed by the first and third axis directions, i.e. both x-axis and z-axis. FIG. 5 shows a cross section of a user in a supine position. When the user is turning around in the bed, the vector $\sqrt{A_x^2 + A_z^2}$ will remain equal to 1 G (in stable position, exactly at flat level). It does not matter in which position the user is lying on the bed (e.g. supine, side, or prone) because the vector $\sqrt{A_x^2 + A_z^2}$ will be 1 G is all cases.

When the user is going to stand up, i.e. in a non-sleeping position, the vector $\sqrt{A_x^2 + A_z^2}$ will decrease to zero because both the x-axis and the z-axis will become parallel to the earth and the acceleration component in the y-axis will increase from 0 to 1 G.

Since an accelerometer has tolerance and may not be calibrated in production, it may be risky to use fixed thresholds. Instead of fixed thresholds, it may be beneficial to use the axis excluded in the vector; in this example the $|A_y|$. So when the $|A_y|$ becomes > vector $\sqrt{A_x^2 + A_z^2}$, the user is supposed to be in a non-sleeping position. When the $|A_y|$ is lower, the user is considered to be in a sleeping position. Toggle moment will be at 45°.

Figure 6:
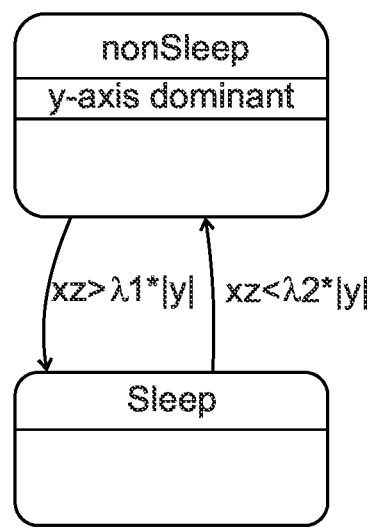
FIG. 6 shows the detection of the sleeping and non-sleeping positions.

In order to remain flexible on the angle of toggling, the threshold may be multiplied based on the y-axis by the tangent of a desired angle. For example, FIG. 6 shows an exemplary algorithm when using 40° and 50° as hysteretic toggle angles for going from sleep to non-sleep position and back. In this example, $\lambda_1 = \tan(50°)$ and $\lambda_2 = \tan(40°)$.

Standing vs Upside Down Position

Figure 7:
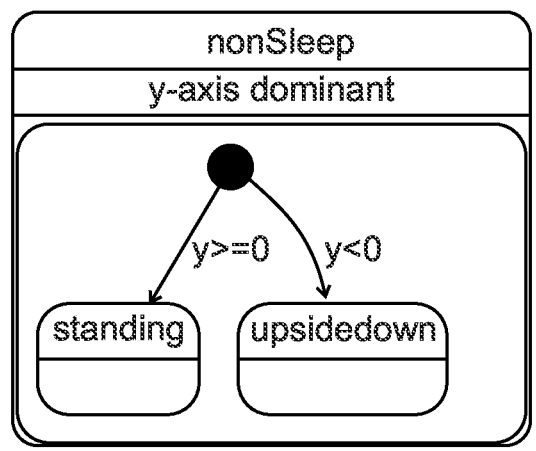
FIG. 7 shows the detection of standing and upside down positions.

When the user is in a non-sleeping position, two variants are possible: standing and upside down. In order to distinguish between upside down and standing positions, the system can look at the value of the second acceleration component $A_y$ in the second axis direction Y. As shown in FIG. 7, when the $A_y$ is positive, the user is standing and when the $A_y$ is negative, the user is upside down.

Flat vs Side Position

Figure 8:
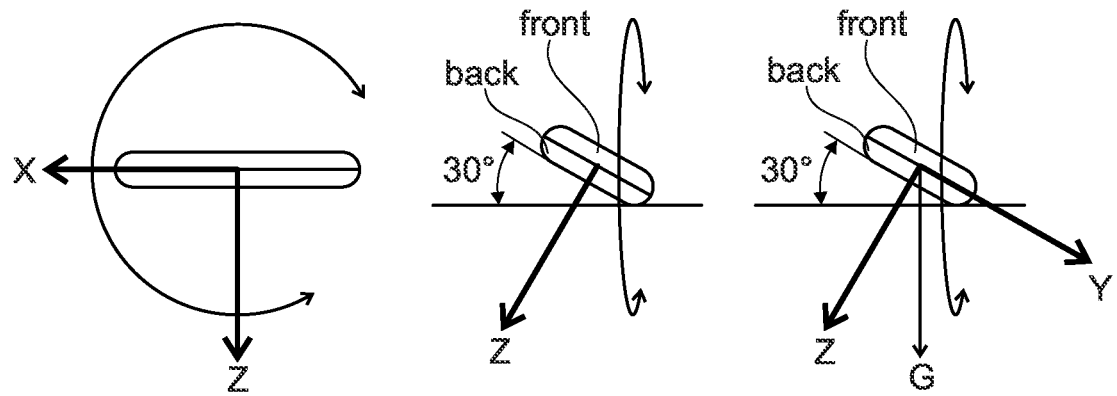
FIG. 8 shows a cross section of a user in an 'ideal' supine position. The middle picture shows a situation where the user is tilted 30°. The right picture shows the compensation of the tilting by using vector $\sqrt{A_x^2+A_z^2}$ for determination between flat and side positions instead of using vector $A_z$ only.

Flat position (supine or prone) and side position (left or right) may be detected by one axis only, for example z-axis. The left image of FIG. 8 shows an 'ideal' supine situation. In this case, the absolute value of the third acceleration component $A_z$ will show the maximum value and the first acceleration component $A_x$ is zero.

However, in some situations, the user may be tilted up to 30° in a horizontal position. In this case, the absolute value of the third acceleration component $A_z$ will already be decreased in that situation as can be seen in the middle picture of FIG. 8. To compensate for that, the vector $\sqrt{A_y^2 + A_z^2}$ can be used as shown in the right picture of FIG. 8 to compare with vector $A_x$.

Figure 9:
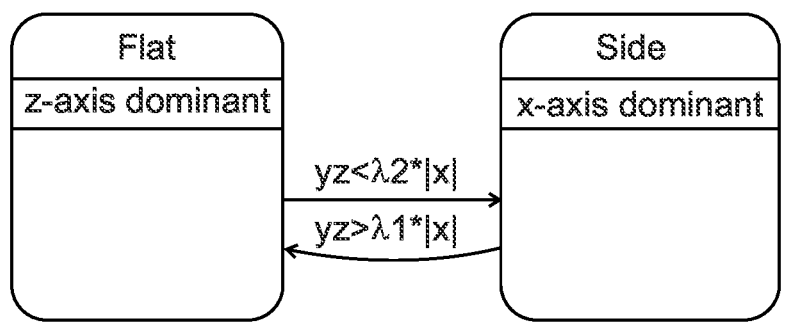
FIG. 9 shows the detection of flat and side positions.

In order to remain flexible on the angle of toggling, the threshold may also be multiplied based on the first acceleration component $A_x$ in the x-axis by the tangent of a desired angle. For example, FIG. 9 shows the algorithm when using 40° and 50° as hysteretic toggle angles for going from sleep to non-sleep position and back. In this example, $\lambda_1 = \tan(50°)$ and $\lambda_2 = \tan(40°)$.

Left vs Right Position

Figure 10:
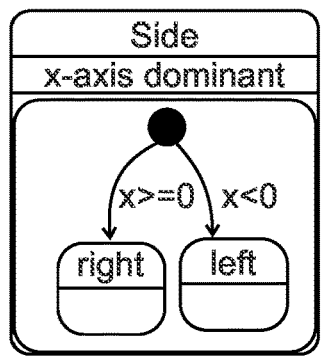
FIG. 10 shows the detection of left and right positions.

When the user is in a side position, two variants are possible: left and right. In order to distinguish between left and right positions, the system can look at the value of the first acceleration component $A_x$. As shown in FIG. 10, when $A_x$ is positive, the user is in a right position. When $A_x$ is negative, the user is in a left position.

Supine vs Prone Position

Figure 11:
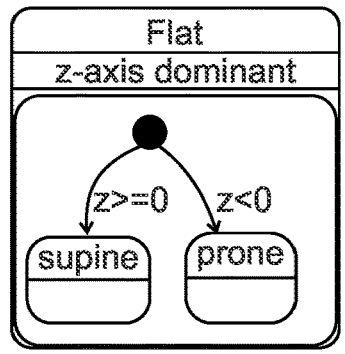
FIG. 11 shows the detection of standing and upside down positions.

When the user is in a flat position, two variants are possible: supine and prone. In order to distinguish between supine and prone positions, the system can look at the value of the third acceleration component $A_z$. As shown in FIG. 11, when $A_z$ is positive, the user is in a supine position, and when $A_z$ is negative, the user is in a prone position.

Full Position Detection

Figure 12:
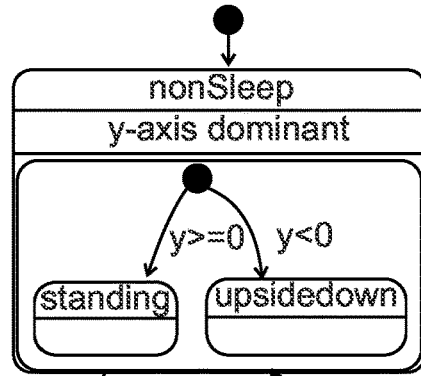
FIG. 12 shows a full position detection.
Figure 12:
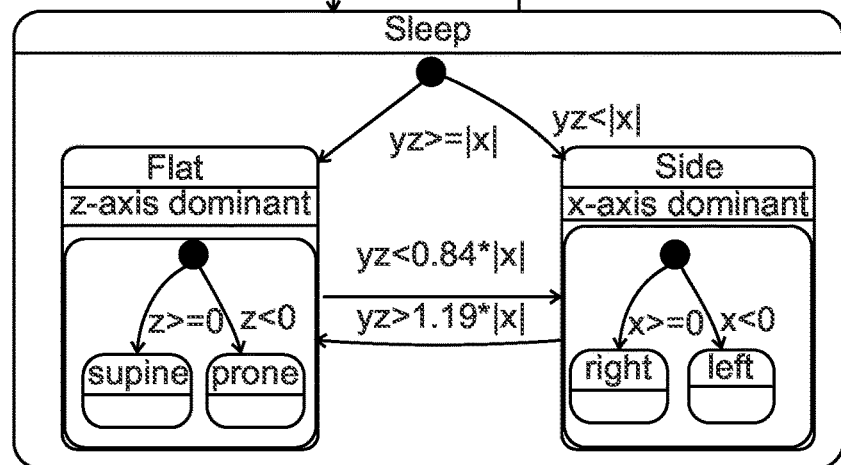

The above-discussed position detections may be combined to give a total algorithm as shown in FIG. 12. In the example shown in FIG. 12, the first priority is set to the detection of sleeping and non-sleeping positions. The second priority is set to the detection of flat and side positions. The last priority is to determine within the three main positions the direction by the sign of a value of one of the three acceleration components.

Movement Detection

Figure 13:
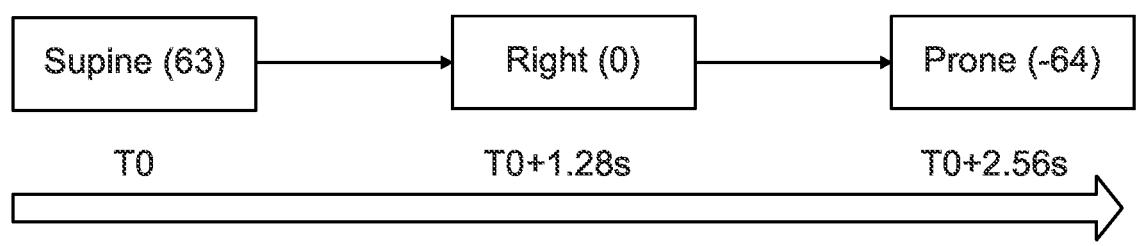
FIG. 13 shows a typical movement within 1 second from supine to prone in case averaging of samples is applied, in accordance with the prior art.

During the testing, the inventors of the present disclosure have discovered that moving from one sleeping position to an opposite position (180°) within 1 second may cause a wrong position detection in case averaging of samples is applied which is intentionally not done in the disclosure. For example, as shown in FIG. 13, rotating device from position 'supine' to position 'prone' within 1 second may cause a wrong position detection and standing position could be signalled to the system. Typical movement (e.g. within about 1 second) from supine to prone may produce the following averaging buffer of the z-axis data ($A_z$). Even if at the final time of the movement the physical position is 'prone' (−63) the averaged value used for position calculation is −1 that stands 'right'. The buffer will soon fill-up with the correct values (−63) and the momentary averaged value will also stabilize at −63 that will give a valid 'prone' position.

In order to solve the above-identified problem, instead of filtering, movement detection is applied. This may prevent the system from calculation with artificial numbers causing a wrong position detection.

The first movement detection may be based on the fact that the resulting vector of all axes should be 1 G when in stable position. The resulting vector can be calculated with:

$$\sqrt{A_x^2 + A_y^2 A_z^2}$$

Movement may be defined when the resulting vector exceeds a threshold, such as:

$$|\sqrt{A_x^2 A_y^2 A_z^2} - 1G| \geq \text{MovingThreshold}$$

Since the first movement detection can be tricked by applying an acceleration of 2 G from the ground. That means that the 1 G directed to ground will become 1 G directed upwards. The vector will remain equal to 1 G and no movement is detected while there is. Therefore, in some examples, a second movement detection may be required.

Figure 14:
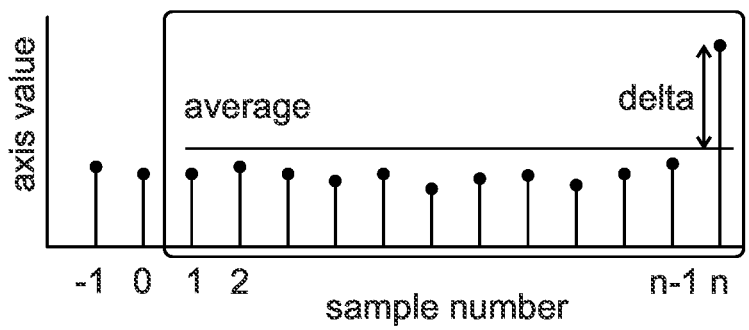
FIG. 14 shows a representation of the second movement detection.

The second movement detection may be based on several consecutive samples that are within a certain range of the moving average. FIG. 14 shows an example. In this case, the average of n samples is calculated, where n is an integer number greater than 1. For each sample, delta between its value and the average is calculated. When all sample values are within a threshold from the moving average, the user is considered as stable. This calculation is performed for x, y and z-axis.

It should also be understood that, unless clearly indicated to the contrary, in any methods claimed herein that include more than one step or act, the order of the steps or acts of the method is not necessarily limited to the order in which the steps or acts of the method are recited.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A computer-implemented method for body position detection, comprising the steps of:
   a) receiving accelerometer data from an accelerometer mounted on a user,
      wherein the received accelerometer data comprises three acceleration components including a first acceleration component in a first axis direction, a second acceleration component in a second axis direction substantially perpendicular to the first axis direction, and a third acceleration component in a third axis direction substantially perpendicular to a plane formed by the first and second axes; and wherein the first axis direction is parallel to a frontal axis of the user, the second axis direction is parallel to a longitudinal axis of the user, and the third axis direction is parallel to a sagittal axis of the user; and b) determining, based on the received accelerometer data, at least one body position based on a comparison between an absolute value of a projection of a gravity vector on a plane formed by two of the first, second, and third axes and an absolute value of an acceleration component in a remaining axis direction.

2. Computer-implemented method according to claim 1, wherein the at least one body position comprises a sleeping position and a non-sleeping position; and wherein step b) further comprises the step of determining whether the user is in a sleeping position or in a non-sleeping position based on a comparison between an absolute value of the projection of the gravity vector on the plane formed by the first and third axis directions and an absolute value of the second acceleration component.

3. Computer-implemented method according to claim 2, wherein the absolute value of the second acceleration component is multiplied by a tangent of a desired angle for the comparison.

4. Computer-implemented method according to claim 2, wherein, when it is determined that the user is in a non-sleeping position, the method further comprises the step of determining, based on a sign of a value of the second acceleration component, whether the user is in a standing or an upside-down position.

5. Computer-implemented method according to claim 2, wherein, when it is determined that the user is in a sleeping position, the method further comprises the step of determining whether the user is in a flat position or in a side position based on (i) a comparison between an absolute value of the third acceleration component with an absolute value of the first acceleration component, or (ii) a comparison between an absolute value of a projection of a gravity vector on a plane formed by the second and third axes and an absolute value of the first acceleration component.

6. Computer-implemented method according to claim 5, wherein the absolute value of the first acceleration component is multiplied by a tangent of a desired angle for the comparison.

7. Computer-implemented method according to claim 5, wherein, when it is determined that the user is in a side position, the method further comprises the step of determining, based on a sign of a value of the first acceleration component, whether the user is in a left or right position.

8. Computer-implemented method according to claim 5, wherein, when it is determined that the user is in a flat position, the method further comprises the step of determining, based on a sign of a value of the third acceleration component, whether the user is in a supine or prone position.

9. Computer-implemented method according to claim 1, further comprising:

detecting, based on the received accelerometer data, a movement of the user; and determining the at least one body position of the user using an unfiltered value of the three acceleration components, if the movement is below a pre-defined threshold.

10. Computer-implemented method according to claim 9, wherein the detection of the movement of the user further comprises:

calculating a resultant vector of the three acceleration components; and determining that the user is moving when the resultant vector exceeds a moving threshold.

11. Computer-implemented method according to claim 9, wherein the detection of the movement of the user further comprises:

calculating an average of a plurality of consecutive samples that are within a certain range of a moving average for each of the three acceleration components;

calculating, for each sample, a difference between a sample value of the respective sample and the average; and determining that the user is moving when one or more sample values exceed a threshold from the moving average.

12. An apparatus comprising
a communications module configured to receive accelerometer data from an accelerometer mounted on a user; and
a processing unit configured to perform the steps of the method according to claim 1.

13. A body position detection system, comprising:
an accelerometer mountable on a user; and
an apparatus according to claim 12.

14. A computer program product comprising instructions to cause the apparatus or the body position detection system to execute the steps of the method according to claim 1.

15. A computer-readable data carrier having stored thereon the computer program product of claim 14.

* * * * *